(12) United States Patent
Bailey (10) Patent No.: US 11,344,437 B2
(45) Date of Patent: May 31, 2022

(54) TRIAL NECK APPARATUS AND METHOD

(71) Applicant: DEPUY IRELAND UNLIMITED COMPANY, County Cork (IE)

(72) Inventor: Andrew Bailey, Leeds (GB)

(73) Assignee: DEPUY IRELAND UNLIMITED COMPANY

( * ) Notice: Subject to any disclaimer, the term of this patent is extended or adjusted under 35 U.S.C. 154(b) by 206 days.

(21) Appl. No.: 16/650,538

(22) PCT Filed: Sep. 11, 2018

(86) PCT No.: PCT/EP2018/074409
§ 371 (c)(1),
(2) Date: Mar. 25, 2020

(87) PCT Pub. No.: WO2019/068427
PCT Pub. Date: Apr. 11, 2019

(65) Prior Publication Data
US 2020/0276029 A1    Sep. 3, 2020

(30) Foreign Application Priority Data

Oct. 3, 2017 (GB) ...................................... 1716107

(51) Int. Cl.
*A61F 2/46* (2006.01)
*A61F 2/36* (2006.01)
*A61F 2/30* (2006.01)

(52) U.S. Cl.
CPC .......... *A61F 2/4684* (2013.01); *A61F 2/3609* (2013.01); *A61F 2002/30845* (2013.01);
(Continued)

(58) Field of Classification Search
CPC ........ A61F 2/4684; A61F 2/36; A61F 2/3609; A61F 2002/3611; A61F 2002/3613;
(Continued)

(56) References Cited

U.S. PATENT DOCUMENTS 4,957,510 A * 9/1990 Cremascoli ........... A61F 2/3662
623/22.46
4,962,155 A  10/1990 Fujita
(Continued)

FOREIGN PATENT DOCUMENTS

CN    1193899 A    9/1998
CN   102048599 A    5/2011
(Continued)

*Primary Examiner* — Alvin J Stewart (57) ABSTRACT

A trial neck (30) and a method for trialling a neck of an orthopedic implant in a hip replacement procedure. The method includes inserting a broach (10) into a medullary canal of a femur and connecting a distal end of a trial neck to a proximal end (12) of the broach. The trial neck includes a proximal end connectable to a trial head. The trial neck includes a body portion extending along a neck axis (5) of the trial neck between the distal end and the proximal end. The proximal end includes a male connector for connection to a corresponding female connector of a trial head. The male connector includes a plurality of connection members (34A, 34B) extending parallel to the neck axis. The connection members are separated by one or more elongate slots (50) including at least one kink (52) forming an interlock between the connection members separated by that slot. The connection members are resiliently deflectable.

11 Claims, 9 Drawing Sheets

(52) U.S. Cl.
CPC .............. *A61F 2002/30985* (2013.01); *A61F 2002/3627* (2013.01); *A61F 2002/3647* (2013.01); *A61F 2002/3652* (2013.01)

(58) Field of Classification Search
CPC ...... A61F 2002/3625; A61F 2002/3627; A61F 2002/365; A61F 2002/3652; A61F 2002/30607; A61F 2002/30614; A61F 2002/30616; A61F 2002/30734; A61B 17/1664; A61B 17/1684; A61B 17/164

See application file for complete search history.

(56) References Cited

U.S. PATENT DOCUMENTS

| | | | |
|---|---|---|---|
| 5,480,451 A | 1/1996 | Grundei | |
| 5,569,263 A | 10/1996 | Hein | |
| 5,645,607 A * | 7/1997 | Hickey | A61B 17/1659 623/23.35 |
| 5,653,764 A * | 8/1997 | Murphy | A61F 2/3609 623/23.15 |
| 5,766,261 A * | 6/1998 | Neal | A61B 17/1659 623/21.15 |
| 5,888,211 A * | 3/1999 | Sanders | A61F 2/4684 623/22.4 |
| 6,197,062 B1 * | 3/2001 | Fenlin | A61F 2/4014 623/19.12 |
| 6,224,605 B1 * | 5/2001 | Anderson | A61B 17/15 606/85 |
| 6,447,518 B1 | 9/2002 | Krause | |
| 6,464,728 B1 | 10/2002 | Murray | |
| 6,702,854 B1 | 3/2004 | Cheal | |
| 6,977,000 B2 * | 12/2005 | Vanasse | A61F 2/4684 623/22.42 |
| 7,135,044 B2 * | 11/2006 | Bassik | A61F 2/4014 623/22.42 |
| 7,572,297 B2 | 8/2009 | Cheal | |
| 7,608,112 B1 * | 10/2009 | Kuczynski | A61F 2/4684 606/102 |
| 7,641,698 B1 | 1/2010 | Gibbs | |
| 7,981,161 B2 | 7/2011 | Choi | |
| 8,048,167 B2 | 11/2011 | Dietz | |
| 8,052,758 B1 * | 11/2011 | Winslow | A61F 2/4657 623/22.42 |
| 8,449,619 B2 * | 5/2013 | Metcalfe | A61F 2/4684 623/22.11 |
| 8,663,333 B2 * | 3/2014 | Metcalfe | A61F 2/4014 623/19.11 |
| 11,197,764 B2 * | 12/2021 | Mutchler | A61F 2/4014 |
| 2002/0193882 A1 * | 12/2002 | Koller | A61F 2/4684 623/23.12 |
| 2003/0074080 A1 * | 4/2003 | Murray | A61F 2/4637 623/22.42 |
| 2004/0004186 A1 | 1/2004 | Jiyan | |
| 2004/0064186 A1 * | 4/2004 | McCleary | A61F 2/4684 623/18.11 |
| 2004/0064188 A1 * | 4/2004 | Ball | A61F 2/4657 623/19.11 |
| 2004/0078079 A1 * | 4/2004 | Foley | A61B 17/025 623/17.11 |
| 2004/0122440 A1 | 6/2004 | Daniels | |
| 2004/0236341 A1 | 11/2004 | Petersen | |
| 2004/0267372 A1 | 12/2004 | Vanasse | |
| 2005/0033443 A1 * | 2/2005 | Blatter | A61F 2/4014 623/19.14 |
| 2005/0107799 A1 | 5/2005 | Graf | |
| 2005/0143828 A1 | 6/2005 | Collins | |
| 2005/0203634 A1 * | 9/2005 | Bassik | A61F 2/4014 623/22.42 |
| 2005/0245934 A1 | 11/2005 | Tuke | |
| 2005/0288792 A1 * | 12/2005 | Landes | A61F 2/4644 623/21.18 |
| 2006/0142871 A1 * | 6/2006 | Biss | A61F 2/4014 623/23.42 |
| 2006/0167557 A1 * | 7/2006 | Terrill | A61F 2/3609 623/22.43 |
| 2006/0241625 A1 * | 10/2006 | Metcalfe | A61B 17/1659 606/79 |
| 2007/0050039 A1 * | 3/2007 | Dietz | A61F 2/3609 623/19.13 |
| 2007/0219641 A1 | 9/2007 | Dorr | |
| 2008/0091274 A1 * | 4/2008 | Murphy | A61F 2/3609 623/22.42 |
| 2008/0133023 A1 * | 6/2008 | Schlotterback | A61F 2/3609 623/22.42 |
| 2008/0200990 A1 * | 8/2008 | McTighe | A61F 2/3662 623/22.42 |
| 2008/0262626 A1 | 10/2008 | Raugel | |
| 2009/0048682 A1 | 2/2009 | Choi | |
| 2009/0054993 A1 * | 2/2009 | Le Bon | A61F 2/4684 623/23.15 |
| 2010/0100193 A1 * | 4/2010 | White | A61F 2/46 623/22.43 |
| 2010/0241239 A1 | 9/2010 | Smith | |
| 2012/0239160 A1 * | 9/2012 | Belew | A61F 2/4684 623/20.35 |
| 2012/0259423 A1 | 10/2012 | Carr | |
| 2012/0265319 A1 * | 10/2012 | Prybyla | A61F 2/34 623/22.36 |
| 2012/0290099 A1 | 11/2012 | Gibson | |
| 2013/0144397 A1 | 6/2013 | Smith | |
| 2013/0158674 A1 | 6/2013 | Chow | |
| 2013/0261762 A1 * | 10/2013 | Kennedy | A61F 2/3609 623/22.42 |
| 2013/0325132 A1 * | 12/2013 | Reignier | A61F 2/4684 623/19.14 |
| 2014/0276866 A1 | 9/2014 | Endsley | |
| 2014/0350691 A1 * | 11/2014 | Linares | A61F 2/3609 623/22.45 |
| 2016/0030200 A1 * | 2/2016 | Hunt | A61F 2/3662 623/20.35 |
| 2016/0175116 A1 * | 6/2016 | Bader | A61F 2/4657 606/86 R |
| 2016/0193050 A1 * | 7/2016 | Cappelletti | A61F 2/3609 623/18.11 |
| 2017/0202685 A1 * | 7/2017 | Rao | A61F 2/4684 |
| 2018/0303551 A1 * | 10/2018 | Hopkins | A61B 17/1778 |
| 2020/0261248 A1 * | 8/2020 | Wills | A61F 2/34 |
| 2020/0352742 A1 * | 11/2020 | Horne | A61B 17/1659 |
| 2021/0093332 A1 | 4/2021 | Walker | |

FOREIGN PATENT DOCUMENTS

| | | |
|---|---|---|
| CN | 106264797 A | 1/2017 |
| DE | 102007032014 B3 | 10/2008 |
| EP | 1435223 A1 | 7/2004 |
| FR | 2574283 A1 | 6/1986 |
| FR | 2796267 A1 | 1/2001 |
| GB | 806441 A | 12/1958 |
| JP | 5859810 B2 | 2/2016 |
| WO | 92/03993 A1 | 3/1992 |
| WO | 1996036284 A1 | 11/1996 |
| WO | 2002026145 A1 | 4/2002 |
| WO | 2009106866 A1 | 9/2009 |
| WO | 2009108683 A1 | 9/2009 |
| WO | 2012035294 A2 | 3/2012 |
| WO | 2014140636 A1 | 9/2014 |
| WO | 2014140639 A1 | 9/2014 |

* cited by examiner

TRIAL NECK APPARATUS AND METHOD

CROSS REFERENCE TO RELATED PCT APPLICATION

This application is a National Stage 35 U.S.C. 371 of International Patent Application PCT/EP2018/074409 filed Apr. 11, 2019, which claims priority to United Kingdom Application No. GB 1716107.6, filed Oct. 3, 2017, both of which are incorporated by reference in their entireties.

FIELD OF THE INVENTION

This invention relates to a trial neck for use in a hip replacement procedure. This invention also relates to a surgical kit for a hip replacement procedure. This invention further relates to a method for trialling a neck of an orthopedic implant in a hip replacement procedure.

BACKGROUND OF THE INVENTION

Hip replacement is a surgical procedure in which the hip joint is replaced by a prosthetic implant. Total replacement of the hip joint involves installing an acetabular cup implant in the acetabulum of a patient and installing a prosthetic in the femur of the patient. The prosthetic typically includes a stem, which is received in the medullary canal of the femur, and a head having a bearing surface which is received in the acetabulum or acetabular cup implant. The prosthetic typically also includes a neck which extends between a proximal end of the stem and the head.

Successful hip replacement surgery requires correct positioning and alignment of the acetabular cup implant as well as the prosthetic itself. Misalignment and/or the selection of an inappropriately sized acetabular cup implant and/or the prosthetic may result is restricted movement of the prosthetic and/or accelerated wear and tear of the bearing surfaces of the acetabular cup implant and the bearing surface of the head. Various factors are involved in achieving this correct positioning and alignment. At least some of these factor relate to the neck of the prosthetic. These factors may include, for instance, the length of the neck, and an angular orientation (offset) of the neck relative to the stem.

Hip replacement surgery usually involves trialling the various components of the acetabular cup implant and the prosthetic. As part of this, various sizes of broach may be used to prepare the medullary canal of the femur. Once the broach is inserted in the femur, a trial neck and trial head may also be attached to the broach, in order to evaluate whether a prosthetic having a neck and head of that type (e.g. in terms of the size and offset of the neck) would appropriate for the patient.

After the surgeon is satisfied that the chosen combination of broach, trial neck and trial head are correctly positioned and aligned, they may be removed and replaced with the implant itself.

U.S. Pat. No. 8,449,619 describes a surgical device that includes a first portion and a second portion. The first and second portions are releasably connected together by cooperating first and second formations. The first formation may be formed on the first portion. The second formation includes a resilient arm which is formed on the second portion and engages the first formation on the first portion. The resilient arm may be integrally formed with the second portion.

US 2006/241625 A1 describes a surgical device that includes a first portion and a second portion. The first and second portions are releasably connected together by cooperating first and second formations. The first formation may be formed on the first portion. The second formation includes a resilient arm which is formed on the second portion and engages the first formation on the first portion. The resilient arm may be integrally formed with the second portion.

WO 1992/003993 A1 describes a modular trial hip replacement system.

US 2010/241239 A1 describes an apparatus and methods of protecting modular implant connection portions. A guard includes an outer sidewall and an inner sidewall defining a cavity that covers a modular implant connection portion. The modular implant connection covered with the guard can facilitate test-fitting of other modular implant components and allows reaming of the tissue around the guard.

EP 1 435 223 A1 describes a trial for use in performing joint arthroplasty fits in a cavity in the canal of a long bone and assists in the performing of a trial reduction in performing joint arthroplasty. The trial includes a stem portion and a neck portion fixedly connected to the stem portion in a plurality of selectable positions with respect to the stem portion.

US 2004/267372 A1 describes a modular trial neck segment that is utilized for trialing a hip prosthesis for a total hip arthroplasty. The modular trial neck segment is preferably, but not necessarily, utilized for trialing a hip prosthesis for a total hip arthroplasty. The trial neck segment includes a mount attachable to a stem or broach, and a neck that is translatable on the mount for providing various neck offsets with respect to the mount and/or broach. Neck offset is changed via movement of the neck in a single plane of motion. This facilitates the use of the subject invention in minimally invasive arthroplasty wherein working dimensions are small. The design replicates the biomechanics of the neck region of the implant. The mount and slidable neck provide a plurality of neck offsets and/or neck lengths for trialing a final prosthesis in a single device.

US 2005/143828 A1 describes a sleeve and method for use with modular orthopedic implants.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a trial neck for use in a hip replacement procedure, the trial neck comprising:

a proximal end;

a distal end connectable to a proximal end of a broach; and a body portion extending along a neck axis of the trial neck between the distal end and the proximal end, wherein the proximal end of the trial neck includes a male connector for connection to a corresponding female connector of a trial head, wherein the male connector comprises a plurality of connection members extending substantially parallel to the neck axis, wherein the connection members are separated by one or more elongate slots, wherein the connection members are resiliently deflectable inwards towards the neck axis on insertion of the male connector into the female connector of the trial head, and wherein the or each slot of the male connector includes at least one kink forming an interlock between the connection members separated by that slot, to prevent over-deflection of the connection members in a direction towards and/or away from the neck axis.

According to another aspect of the invention, there is provided a method for trialling a neck of an orthopedic implant in a hip replacement procedure, the method comprising:

inserting a broach into a medullary canal of a femur of a patient;

connecting a distal end of a trial neck to a proximal end of the broach, the trial neck comprising:
  said distal end;
  a proximal end; and
  a body portion extending along a neck axis of the trial neck between the distal end and the proximal end,
  wherein the proximal end of the trial neck includes a male connector for connection to a corresponding female connector of a trial head, wherein the male connector comprises a plurality of connection members extending substantially parallel to the neck axis, wherein the connection members are separated by one or more elongate slots, and wherein the connection members are resiliently deflectable inwards towards the neck axis, and
  wherein the or each slot of the male connector includes at least one kink forming an interlock between the connection members separated by that slot, to prevent over-deflection of the connection members in a direction towards and/or away from the neck axis; and connecting the trial head to the male connector of the trial neck by inserting the connection members into the female connector of the trial head, whereby the connection members of the male connector of the proximal end of the trial head are resiliently deflected inwards towards the neck axis.

The plurality of resiliently deflectable connection members of the male connector can provide a convenient and secure way in which to attach the trial neck to the trial head. The interlock between the connection members separated by a given slot, formed by the at least one kink, can prevent over-deflection of the connection members in a direction towards and/or away from the neck axis.

The body portion may include a frame having a plurality of arms extending along the neck axis between the distal end and the proximal end of the trial neck. This arrangement can provide a lightweight construction for the body portion while retaining sufficient structural strength.

Each connection member of the male connector may be integrally formed with a proximal end of one or more respective arms of the body portion. Each elongate slot of the male connector may open out into one or more windows located between the arms of the frame. The arms of frame may themselves be resiliently deflectable, allowing the aforementioned connection members to deflected as mentioned previously.

The male connector may have exactly two connection members. The frame of the body portion may have exactly four arms. In such examples, each connection member may be integrally formed with two of the arms.

A central part of the body portion may be visible between the arms of the frame. This can improve visibility of the various components of the trial head or broach to the surgeon.

The distal end of the trial neck may include a base having a distally facing underside connectable to the proximal end of the broach. The arms of the body portion may extend proximally from the base towards the proximal end of the trial neck. The arms of the body portion may be integrally formed with the base. The base can provide a stable platform for the arms. In some examples, the base and the arms of the frame may form a live hinge for resilient deflection of the connection members of the male connector towards the neck axis as mentioned previously.

The at least one kink may form a zigzag-shaped interlock.

The trial neck may be manufactured by 3D printing. 3D printing lends itself to the relatively intricate features of the trial head, such as the elongate slot and the arms of the frame of the body portion.

According to a further aspect of the invention, there is provided a surgical kit for a hip replacement procedure, the kit comprising:

one or more trial necks according of the kind set out above, wherein at least two of the trial necks are a different size and/or have a different neck offset;
  one or more said broaches; and
  one or more said trial heads.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

FIGS. 1 to 13 show various views of a trial neck 30 according to an embodiment of this invention. In FIGS. 1 to 4 and 13, the trial neck 30 is shown connected to a broach 10, while in FIGS. 5 to 12, the trial neck 30 is shown in isolation.

The trial neck 30 has a proximal end. The proximal end may be connectable to a trial head (not shown), for use in the trialing stage of a hip replacement procedure. As is known in the art, the trial head may include a bearing surface, for insertion into the acetabulum of the patient (or into a trial cup that is placed in the acetabulum as part of the trialing process). The trial neck 30 also has a distal end. The distal end of the trial neck 30 is connectable to a proximal end 12 of the broach 10, as can be seen from FIGS. 1 to 4 and 13.

The trial neck 30 also includes a body portion. The body portion extends between the distal end and the proximal end of the trial neck 30. The body portion may extend along a neck axis 5 (see the dotted line in FIG. 7) of the trial neck 30.

The body portion of the trial neck 30 may be substantially hollow. This can reduce the weight of the trial neck 30, and may also reduce manufacturing costs by reducing that amount of material that is required to construct the trial neck 30. The trial neck 30 may be manufactured using Metal Injection Moulding (MIM), additive manufacturing methods or 3D printing. 3D printing lends itself to the relatively intricate features of the trial neck 30, to be described in more detail below. It is envisaged that the trail neck 30 may be manufactured from Stainless Steel (e.g. 17/4 Stainless Steel).

The body portion of the trial neck 30 may comprise a frame having a number of arms 32. In the present embodiment, the frame has four arms 32, with each arm 32 being located at a respective corner of the trial neck 30, when viewed along the neck axis 5. The arms 32 may extend along the neck axis 5, between the distal end and the proximal end of the trial neck 30. As may be seen from, for example, FIG. 7, although the arms 32 may extend substantially along the neck axis 5, they need not be oriented exactly parallel to the neck axis 5.

In the present embodiment, the arms 32 each extend proximally from a base 36 located at the distal end of the trial neck 30. The arms 32 may be integrally formed with the base 36. The base 36 includes a distally facing underside 37, which engages with and sits flush against a proximally facing surface 14 of the broach 10, when the trial neck 30 and the broach 10 are correctly connected together. The distally facing underside 37 may, in some examples, have a plurality of grooves. These grooves may reduce the surface contact between the base 36 of the trial neck 30 and a build plate of a 3D print machine during manufacture. By doing this it may be possible to reduce the amount of work required to remove the part from the 3D printer, thereby reducing manufacturing costs. The connection of the trial neck 30 to the broach 10 may be implemented using a number of further features, which will be described in more detail below.

In accordance with an embodiment of this invention, central part of the body portion may be visible between the arms of the frame 32, which can improve visibility of the various components of the trial neck 30 or broach 10 to the surgeon. This may be implemented using a number of windows 40, which are located in between, and which are defined by, respective neighbours pairs of arms 32 of the frame. For instance, in the present embodiment, the frame includes:

two medially located arms 32 defining a medial window 40A, two laterally located arms 32 defining a lateral window 40B, an anterior window 40C defined by an anteriorly located one of said medially located arms 32 and an anteriorly located one of said laterally located arms 32, and a posterior window 40D defined by a posteriorly located one of said medially located arms 32 and a posteriorly located one of said laterally located arms 32.

The medial, lateral, anterior and posterior windows 40A-D may allow the central part of the body portion to be seen from medial, lateral, anterior and posterior viewpoints, respectively.

The positions of the windows 40A-D noted above assume that the trial neck 30 is to be used for a hip replacement procedure on the right leg of a patient. Were the trial neck 30 to be used in a hip replacement procedure on a patients left leg, it will be appreciated that the windows would be differently oriented. In particular, the anterior window 40C would become the posterior window and the posterior window 40D would become the anterior window.

In the present embodiment, the proximal end of the trial neck 30 includes a male connector for connection to a corresponding female connector of a trial head. The male connector may be substantially cylindrical. The male connector may have a slight taper so that it is narrower at its proximal end than at its distal end (forming a substantially frustoconical outer surface as shown in the Figures). The inner surface of the female connector of the trial head may be shaped to conform with the shape of the male connector of the trial neck 30, when the trial neck 30 and the trial head are connected together.

The male connector includes a plurality of connection members 34, e.g. two connection members 34A, 34B as shown in the Figures. Each connection member 34 extends substantially parallel to the neck axis 5. The connection members 34 may each extend proximally from the proximal end(s) of one or more of the arms 32 of the frame of the substantially hollow body portion, and may be integrally formed with those arms 32. For instance, in the Figures it can be seen that a first of the connection members 34A is integrally formed with, and extends proximally from, the two arms 32 of the frame that define the medial window 40A, while a second of the connection members 34B is integrally formed with, and extends proximally from, the two arms 32 of the frame that define the lateral window 40B.

Although the example shown in the Figures includes two connection members 34A, 34B, it is envisaged that more than two such connection members may be provided. For instance, the male connector may include four connection members 34, each one being integrally formed with, and extending proximally from a respective one of the arms 32 of the frame.

Each connection member 34 may be separated from each neighbouring connection member 34 of the male connector by an elongate slot. In the present embodiment, which includes two connection members 34A, 34B, the male connector has a single elongate slot 50 separating them. However, it is envisaged that more than one elongate slot of this kind may be provided. For instance, where the male connector includes four connection members 34 as noted above, the male connector may include a first slot separating the medially located connection members from the laterally located connection members and a second elongate slot for separating the anteriorly located connection members from the posteriorly located connection members.

Figure 1:
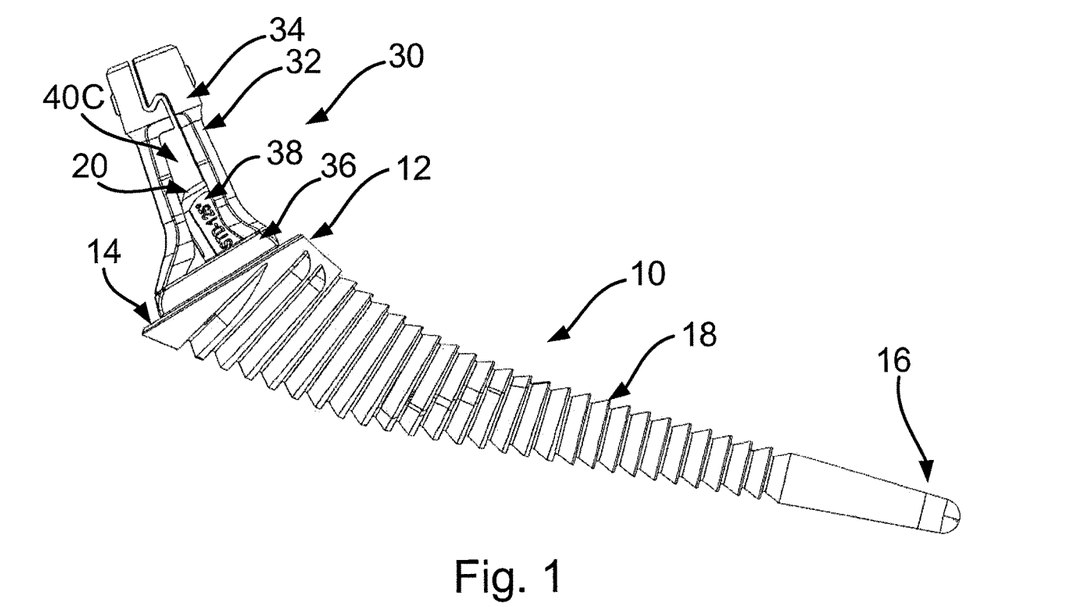
FIG. 1 shows a trial neck and broach connected together in accordance with an embodiment of the invention.
Figure 2:
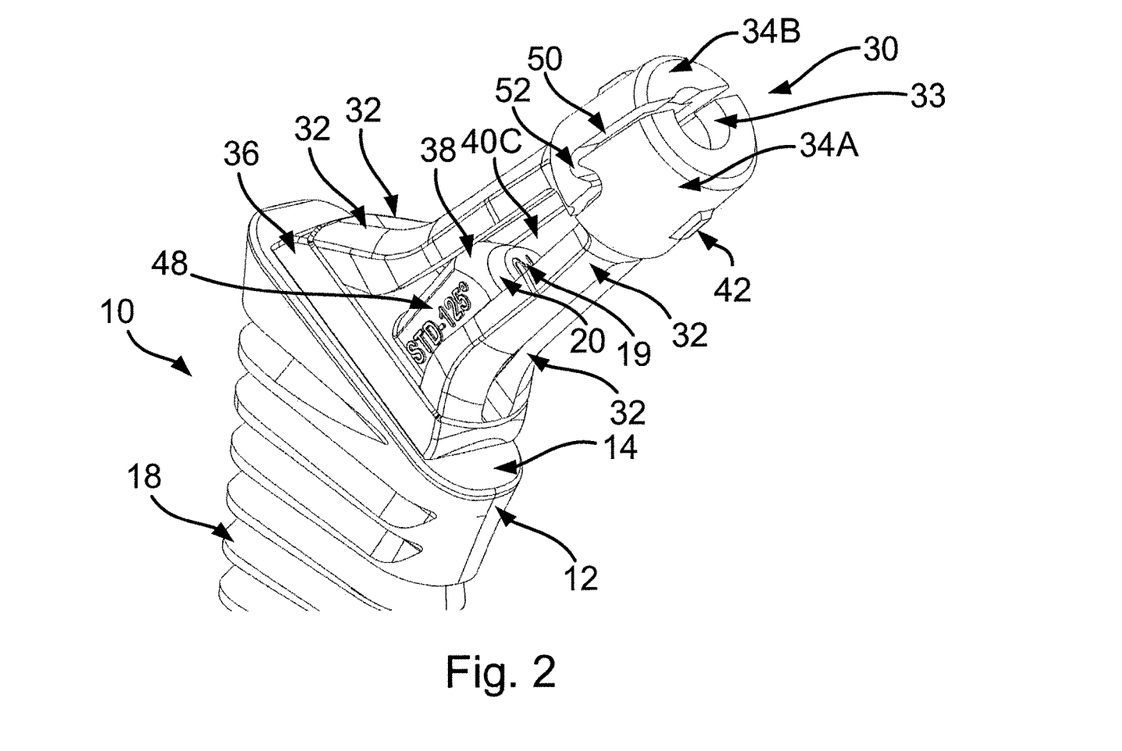
FIG. 2 shows another view of the trial neck and broach of FIG. 1 in accordance with an embodiment of the invention.
Figure 3:
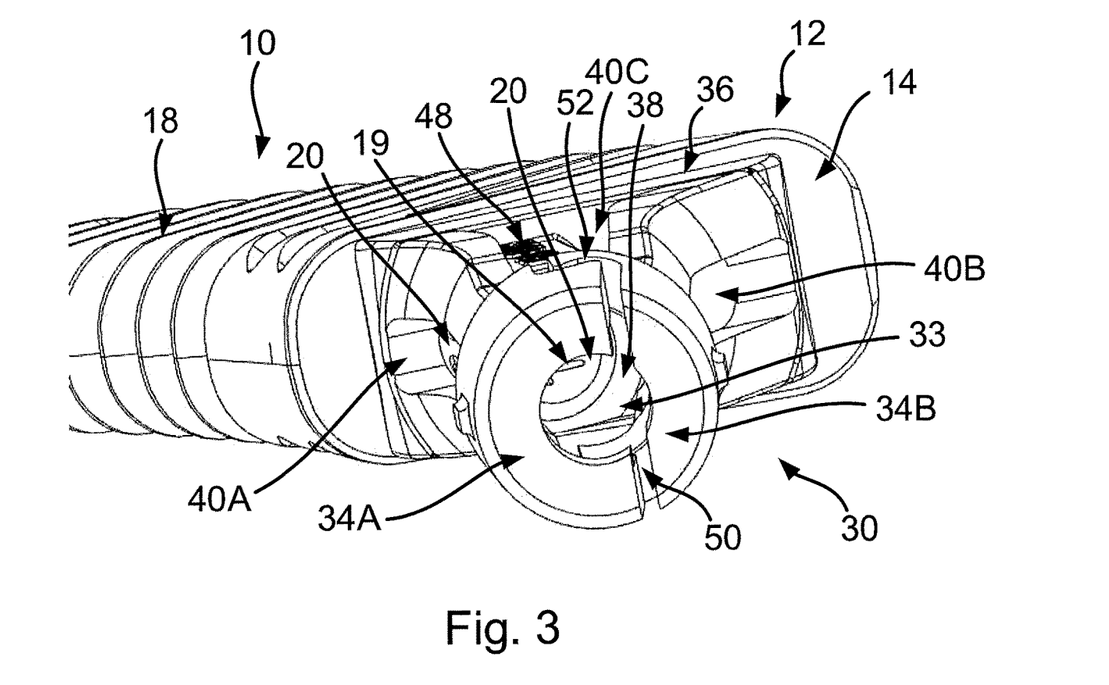
FIG. 3 shows a further view of the trial neck and broach of FIG. 1 in accordance with an embodiment of the invention.
Figure 4:
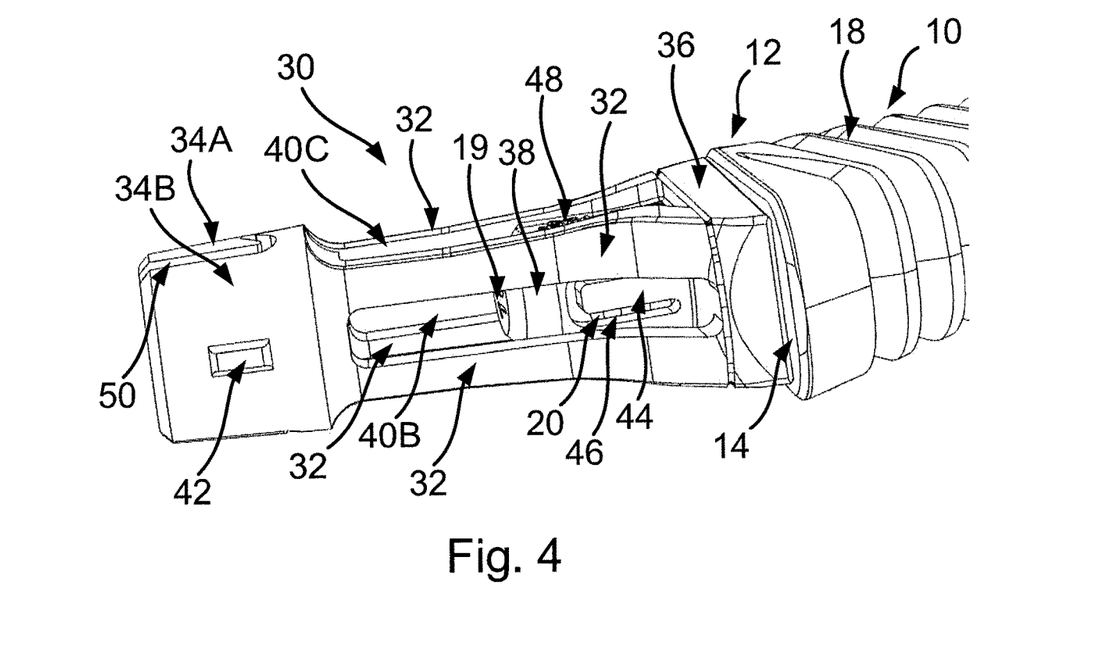
FIG. 4 shows another view of the trial neck and broach of FIG. 1 in accordance with an embodiment of the invention.
Figure 5:
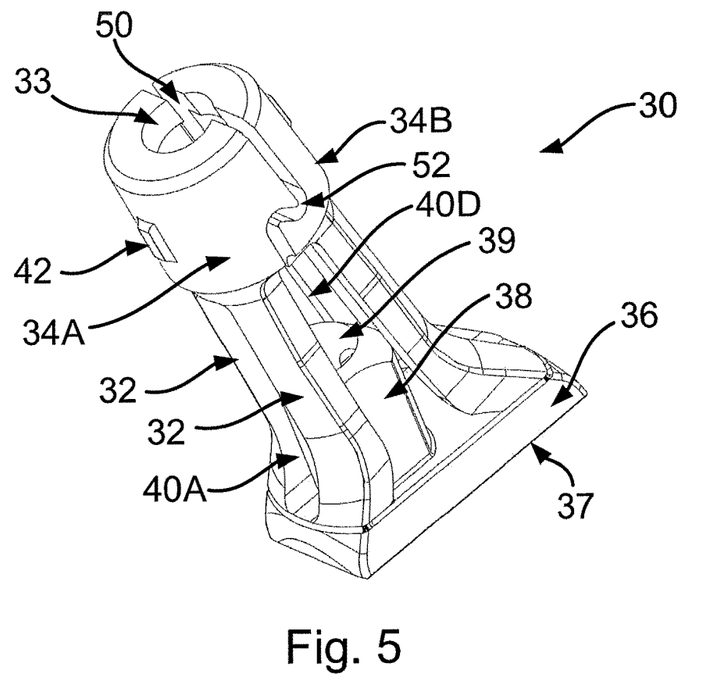
FIG. 5 shows a trial neck in accordance with an embodiment of the invention.
Figure 6:
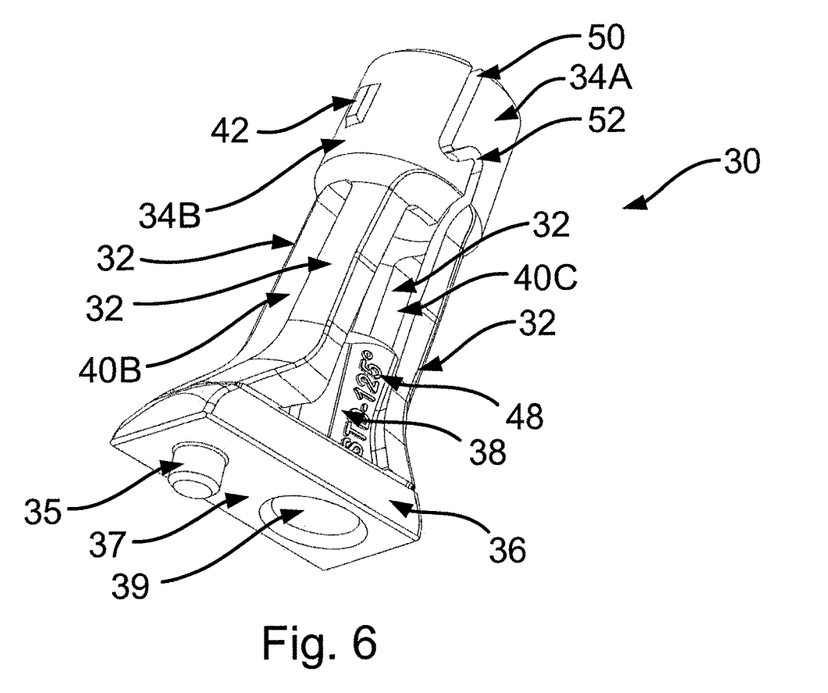
FIG. 6 shows another view of the trial neck of FIG. 5 in accordance with an embodiment of the invention.
Figure 7:
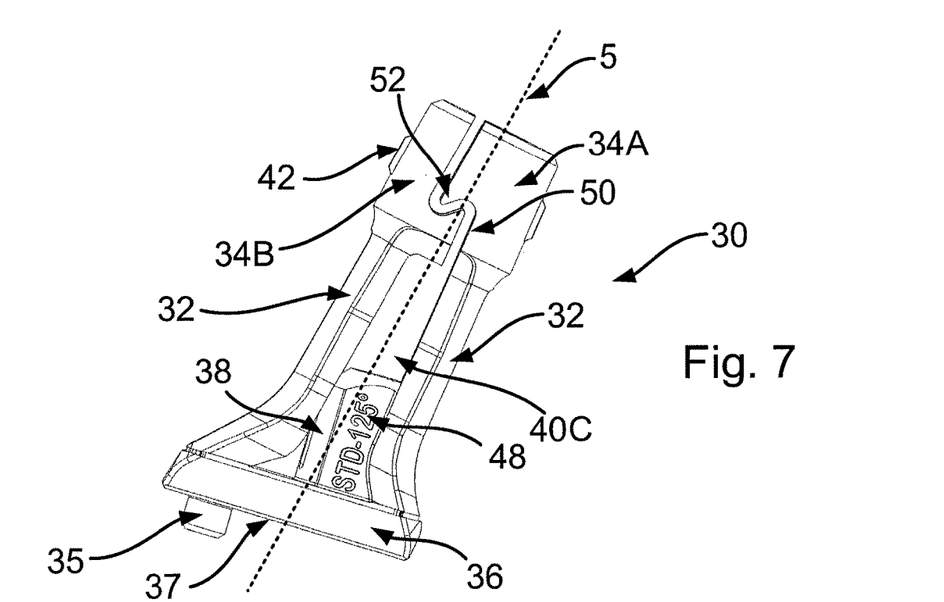
FIG. 7 shows a further view of the trial neck of FIG. 5 in accordance with an embodiment of the invention.
Figure 8:
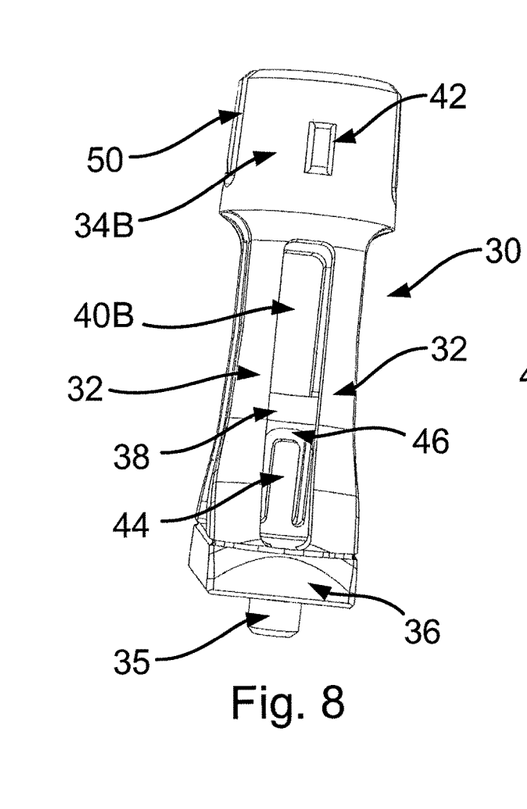
FIG. 8 shows another view of the trial neck of FIG. 5 in accordance with an embodiment of the invention.

As can be seen in FIG. 7, the elongate slot 50 may extend substantially along the neck axis 5. In accordance with an embodiment of this invention, the connection members 34A, 34B may be resiliently deflectable inwards towards the neck axis 5 on insertion of the male connector into the female connector of a trial head. The elongate slot(s) 50 provides space between the connection members 34 to allow this inward deflection to take place. The resilient inward deflection of the connection members 34 may reduce the dimension of the male connector in a direction perpendicular to the neck axis 5, allowing the male connector to be received within the female connector of the trial head. When received in the female connector, the resiliently deflected connection members 34 of the male connector may urge outwardly in a direction perpendicular to the neck axis 5, to urge against the inner surfaces of the female connector, for inhibiting removal of the trial head from the trial neck 30. As can be seen in the Figures, a proximal end of the male connector may be tapered (e.g. chamfered) to aid initial insertion of the connection members 34 into the female connector of the trial head.

In some examples, the outer surfaces of the connection members 34 may include one or more connections features such as the protuberances 42 shown in the Figures. These further connection features may engage with corresponding connection features of the female connector of a trial head, in order to make the connection between the male connector of the trial neck 30 and the female connector of the trial head more secure.

As noted above, the connection members 34A, 34B may each extend proximally from one or more of the arms 32 of the frame of the substantially hollow body portion. In this respect, it is envisaged that the arms 32 may themselves be resiliently deflectable. This can lengthen the lever arm associated with the resilient deflection of the connection members 34, making them easier to deflect while retaining a robust construction for the trial neck 30. For instance, in the present embodiment, the lever arm associated with the connection member 34A extends between the part of the base 36 from which the two arms 32 that define the medial window 40A extend, and the connection member 34A, while the lever arm associated with the connection member 34B extends between the part of the base 36 from which the two arms 32 that define the lateral window 40B extend, and the connection member 34B.

To allow correct inward deflection of the connection members 34A, 34B by deflection of the arms 32 of the frame, each elongate slot 50 may open out into one or more of the windows 40 that are located between the arms 32. For instance, in the present embodiment, the slot 50 opens out into the anterior window 40C on an anterior side of the trial neck 30 and the slot 50 also opens out into the posterior window 40D on a posterior side of the trial neck 30. Where the male connector includes four connection members 34 and two slots as noted above, it is envisaged that one of the slots may open out into anterior window 40C and the posterior window 40D as shown in the Figures, while another of the slots may open out into the medial window 40A on a medial side of the trial neck 30 and may also open out into the lateral window 40B on a lateral side of the trial neck 30.

The above described configuration of the base 36, the arms 32 of the frame and the connection members 34 may thus form a live hinge for resilient deflection of the connection members 34 of the male connector towards the neck axis 5.

In accordance with an embodiment of this invention, the or each slot 50 of the male connector may include one or more kinks 52. Each kink 52 may act as an interlock between the connection members 34 separated by that slot 50, to prevent over-deflection of the connection members 34 in a direction towards and/or away from the neck axis 5. For instance, with reference to FIG. 7, it can be seen that the kink 52 may prevent the connection members 34 being deflected too far away from each other (outwardly, with respect to the neck axis 5) as this would cause the parts of the kink 52 located on either sidewall of the slot 50 to catch on each other. Also, it can be seen that the kink 52 may prevent the connection members 34 being deflected too far towards each other (inwardly, with respect to the neck axis 5) as this would again cause the parts of the kink 52 located on either sidewall of the slot 50 to catch on each other.

In the present example, the trial neck 30 includes two connection members 34 and a single slot 50, the slot having a kink 52. In this example, it will be appreciated that the kink 52 acts to prevent over-deflection of the connection members 34 primarily in a lateral or medial direction. Where the male connector includes four connection members 34 and two slots as noted above, it is envisaged that a kink 52 of one of the slot that opens out into the anterior window 40C and the posterior window 40D may prevent over-deflection of the connection members 34 primarily in a lateral or medial direction as described above, while a kink 52 of one of the slots that opens out into the medial window 40A and the lateral window 40B may prevent over-deflection of the connection members 34 primarily in an anterior or posterior direction.

In the present embodiment, the kink 52 forms a zigzag-shaped (e.g. Z-shaped) interlock. In particular, the outer parts of the "Z" shaped interlock formed by the kink 52 may extend substantially along the neck axis 5, while the middle part of the "Z" shaped interlock may extend at an angle (e.g. 45 degrees) with respect to the outer parts of the "Z" and the neck axis 5. It is envisaged that the kink 52 may form an interlock having a different shape, however. For instance, the kink 52 may form a dove-tailed interlock, in which a dove-tail shaped member on a first side of the slot 50 is received in a correspondingly shaped opening on a second side of the slot 50 opposite the first side.

As noted previously, the distal end of the trial neck 30 is connectable to the broach 10. The broach 10 may include a distal end having a tip 16. The broach 10 may have a proximal end 12 having a proximally facing surface 14. As is known in the art of hip replacement surgery, the broach may have an outer surface having a plurality of teeth 18 or other cutting edges. These may be used by the surgeon when preparing the medullary canal of the femur to receive the stem of a femoral implant.

Examples of the connection of the trial neck 30 to the broach 10 will now be described.

In accordance with an embodiment of this invention, the trial neck 30 includes a resilient retaining member that is configured to engage (e.g. urge against) a surface of the broach 10 when the trial neck 30 is connected to the broach 10. The resilient retaining member can inhibit removal of the trial neck 30 from the broach 10.

The trial neck 30 in this embodiment includes a bore 39. The bore 39 has an open end that is located on the distally facing underside 37 of the distal end of the trial neck 30. The bore 39 is configured to receive a corresponding spigot 20 of the broach, for connecting the trial neck 30 to the broach 10. The spigot 20 extends proximally from the proximally facing surface 14 of the proximal end of the broach 10. In the present embodiment, the above mentioned resilient retaining member comprises a resilient retaining finger 44, which is located on a sidewall of the bore 39 and which biased inwards towards an axis of the bore 39. The resilient retaining member is configured to engage with (e.g. urge against) the spigot 20 when the spigot 20 is received within the bore 39, to inhibit removal of the spigot 20 from the bore 39 and thereby to inhibit removal of the trial neck 30 from the broach 10.

The retaining finger 44 may be integrally formed with the sidewall of the bore 39 (whereby the sidewall of the bore 39 and the resilient retaining finger 44 form a live hinge). This can increase the strength and robustness of the resilient retaining finger 44 and allow the trial neck 30 to be formed of a single piece, without requiring the assembly of separate parts. As noted previously, the trial neck 30 may be manufactured using 3D printing.

As noted previously, the body portion of the trial neck 30 may include a frame having a number of arms 32 and this arrangement may allow a central part of the body portion to be viewed between the arms 32. In accordance with an embodiment of this invention, the resilient retaining member may be located inside the body portion and may be visible between the arms 32 of the frame. For instance, with reference to the Figures, it can be seen that prior to the connection of the trial neck 30 to the broach 10, the resilient retaining finger 44 is visible through at least the medial window 40A and the lateral window 40B (e.g. see FIGS. 8 and 9). In some examples, a proximal end of the bore 39 may open out into the central part of the body portion. In such examples, the interior of the bore 39 may be viewable through the anterior window 40C and posterior window 40D (as well as through the medial window 40A and the lateral window 40B), whereby the resilient retaining finger 44 may also be visible through the anterior window 40C and posterior window 40D.

The ability to view connection features such as the resilient retaining member (e.g. resilient retaining finger 44) and/or the interior of the bore 39 between the arms 32 of the frame of the body portion can assist the surgeon in inspecting the features that are used to connect the trial neck 30 and broach 10 together. This can allow, for instance the surgeon to view the spigot 20 as it enters the bore 39 and also to inspect the spigot 20 and/or bore 39 when the spigot 20 is fully received within the bore 39, allowing him or her to ensure that the connection between these parts is correctly made. Incorrect connection of the trial neck 30 and the broach 10 (e.g. due to the presence of bone fragments between the distally facing underside 37 and the proximally facing surface 14, or inside the bore 39) may otherwise lead to misalignment of the trial neck 30.

Figure 9:
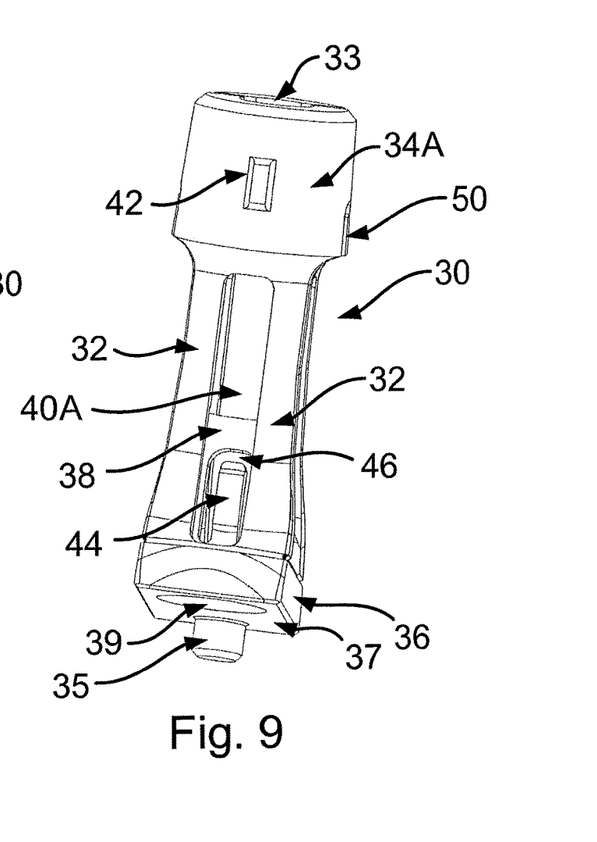
FIG. 9 shows a further view of the trial neck of FIG. 5 in accordance with an embodiment of the invention.
Figure 10:
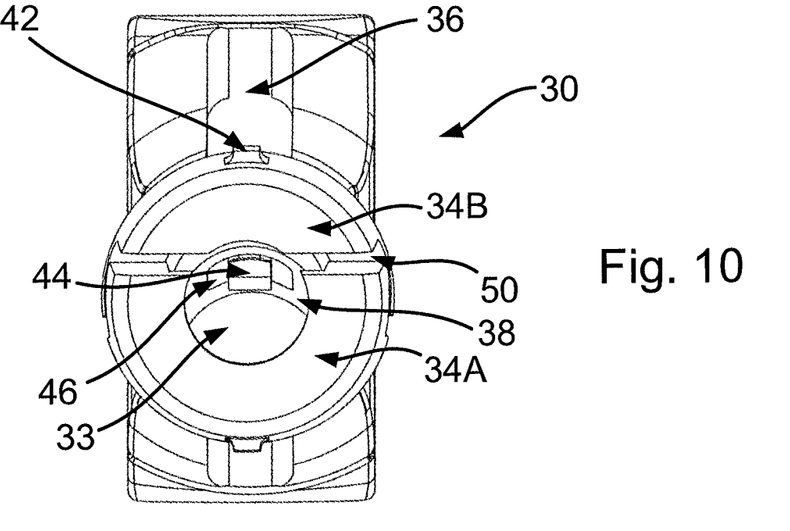
FIG. 10 shows another view of the trial neck of FIG. 5 in accordance with an embodiment of the invention.
Figure 11:
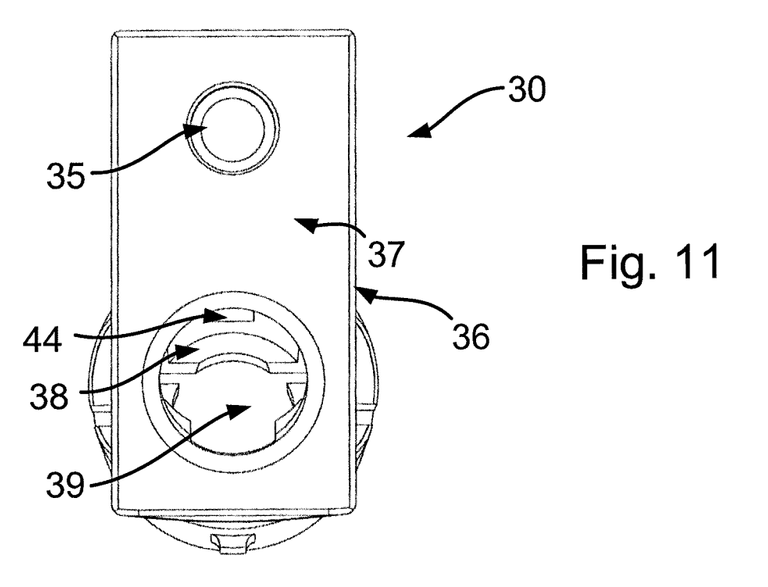
FIG. 11 shows a further view of the trial neck of FIG. 5 in accordance with an embodiment of the invention.
Figure 12:
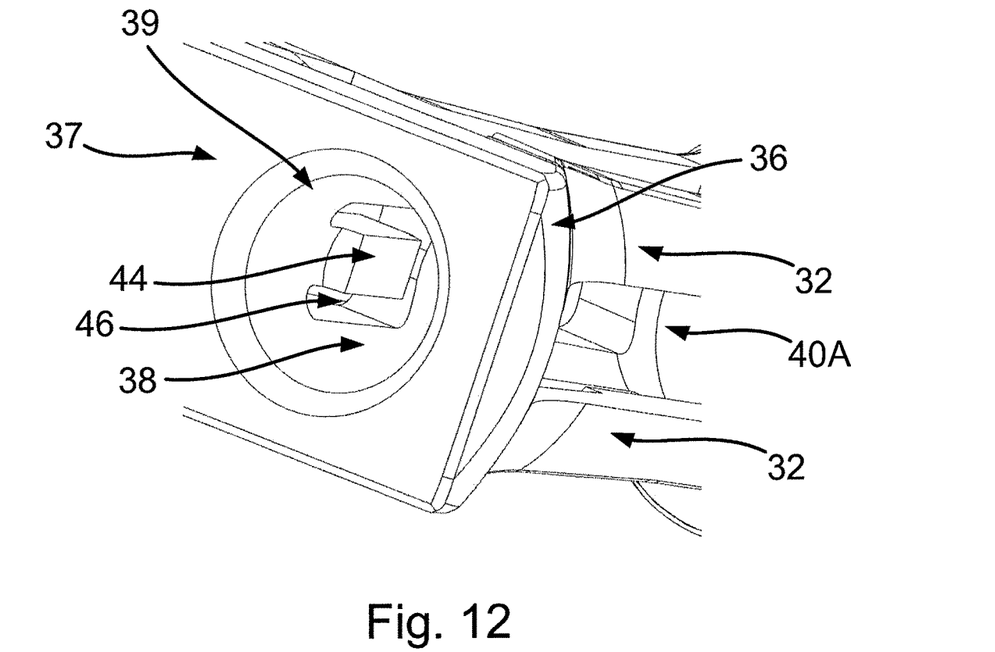
FIG. 12 shows another view of the trial neck of FIG. 5 in accordance with an embodiment of the invention.
Figure 13:
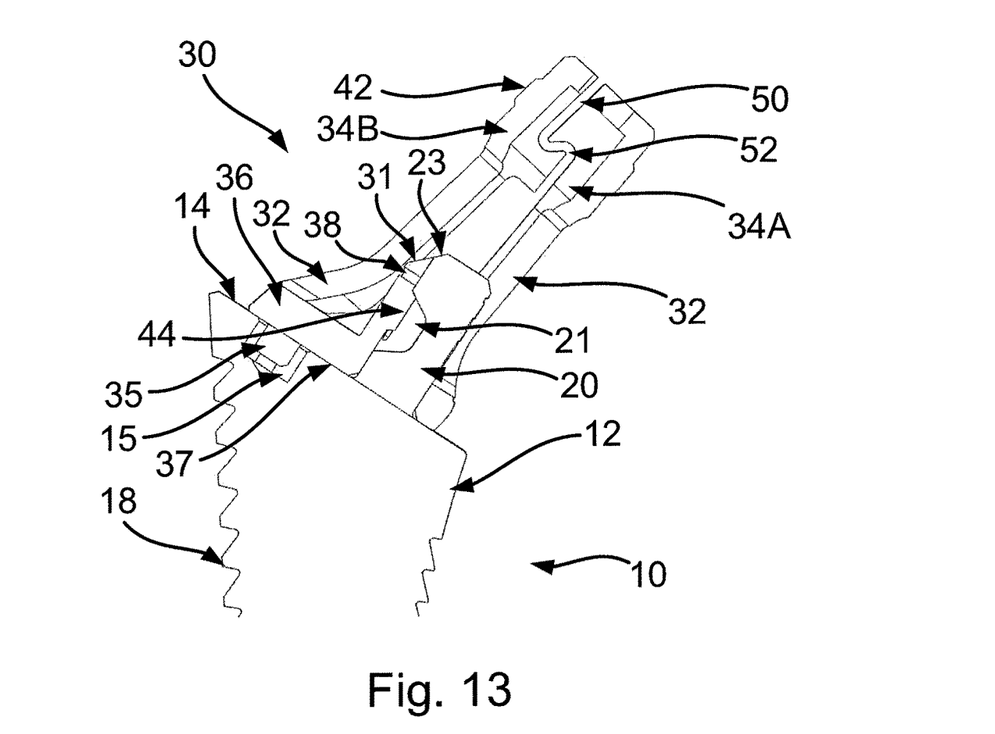
FIG. 13 shows a cross section of the trial neck and broach of FIG. 1 connected together in accordance with an embodiment of the invention.

In the present embodiment, the bore 39 is located within a boss 38 that is itself located in the central part of the body portion. The boss 38 may extend proximally from the distal end (e.g. from the base 36) of the trial neck 30. As can be seen in the Figures, the boss 38 is visible between the arms 32 of the frame. The resilient retaining finger 44 may be provided by forming a U-shaped slot 46 in a side of the boss 38. The boss 38 may, in some embodiments be open on one side of the bore 39 (e.g. the side of the bore 39 opposite the side that incorporates the resilient retaining finger 44, as can be seen in FIGS. 9 and 13). This can further improve the visibility to the surgeon of the connection features of the trial neck 30 and the broach 10. For instance, from FIGS. 9 and 13 it may be appreciated that the interior of the bore 39 may be visible through the medial window 40A and the opening at the side of the boss 38, allowing the surgeon to inspect the interior of the bore 39 for the presence of bone fragments or other materials, and/or to view the spigot 20 as it enters the bore 39.

As can be seen in FIG. 13, the spigot 20 extending from the proximal end 12 of the broach 10 may have a sidewall that includes a notch 21. The notch 21 faces the resilient retaining member. In some embodiments, the notch 21 may be configured to receive the resilient retaining member when the spigot 20 is received within the bore 39. This can provide a more secure connection between the trial neck 30 and the broach 10 than examples in which the resilient retaining member simply urges against a sidewall of the spigot 20.

In some embodiments, the spigot 20 of the broach 10 may be dimensioned such that when the trial neck 30 is correctly connected to the broach 10, a surface of a proximal end of the spigot 20 is flush with a surface of the trial neck 30 in which the second (proximal) open end of the bore 39 is formed. For instance, the spigot 20 may be sized and shaped such that the above mentioned surfaces are flush when the distally facing underside 37 of the distal end of the trial neck 30 is fully seated on the proximally facing surface 14 of a proximal end of the broach 10. In this way, the surgeon may check for the correct connection of the trial neck 30 to the broach 10 by inspecting the above mentioned surfaces to verify that they are flush. The surgeon may visually inspect these surfaces between the arms 32 of the frame and/or may run a finger over the join between them to feel whether they are indeed flush. If these surfaces are not flush this may mean, for example, that the spigot 20 is not fully inserted into the bore 39 (e.g. a fragment of bone or other material located in the bore 39 or in between the distally facing underside 37 and the proximally facing surface 14 may be preventing this).

In the present embodiment, the aforementioned surfaces, which are flush if the trial neck 30 is correctly connected to the broach 10, include a chamfered surface 23 located at a proximal end of the spigot 20 and an angled (e.g. chamfered) surface 31 located at the proximal end of the boss 38 (see FIG. 13). As can be seen in the Figures, the angle of the chamfered surface 23 may be chosen to match the angle of the angled surface 31 located at the proximal end of the boss 38.

In some examples, the proximal end of the spigot 20 may include an indicium 19 of the broach type (e.g. the size of the broach). The indicium 19 may comprise embossed or debossed text. The indicium 19 may, for example, be an alphanumeric indicium. Since the central part of the body portion is visible between the arms 32 of the frame, the indicium 19 may be visible between the arms 32 of the frame when the trial neck 30 is connected to the broach 10. In this way, the surgeon can be conveniently provided with information about the broach 10 while viewing the trial neck 30.

The configuration of the body portion of the trial neck 30, in which a central part thereof is visible between the arms 32 of the frame, may provide additional surfaces (namely, surfaces located in the central part) upon which indicia may be located to provide useful information to the surgeon. The at least one indicium of the trial neck 30 may be visible between the arms 32 of the frame, allowing the surgeon to view them when inspecting the trial neck 30. The at least one indicium may be indicative of the type, size or angular offset of the trial neck 30, and may be an alphanumeric indicium. As with the indicium 19 located on the spigot 20, the at least one indicium of the trial neck 30 may comprise embossed or debossed text. For instance, as can be seen in FIGS. 1, 2, 6 and 7, an indicium 48 may be located on an outer side wall of the boss 38. In the present example, the indicium 48 is visible through the anterior window 40C, although in other examples it may be located in a position on the boss 38 that is visible through another of the windows 40. It is also envisaged that one or more such indicia may be located elsewhere in the central part of the body portion, e.g. on an inwardly facing side wall of one of the arms 32, or on a proximally facing surface of the base 36.

As described below, the trial neck 30 may include features that aid in cleaning it before and/or after its use in a hip replacement procedure. For instance, the above described windows 40 can provide easy access for cleaning fluids to reach the central part of the body portion, to allow any features located in the central part (e.g. the boss 38, the proximally facing entrance to the bore 39 and a proximally facing surface of the base 36) to be cleaned effectively.

In some embodiments, the proximal end of the trial neck 30 may include an opening 33. The opening 33 may, as shown in the Figures, be located in between the connection members 34. The opening 33 may be defined by inwardly facing surfaces (that is to say, surfaces of the connection members 34 that face the neck axis 5) of the connection members 34. The opening 33 may be in fluid communication with the central part of the body portion. This may provide a further route for cleaning fluids to reach the central part of the body portion, further improving the cleanability of the trial neck 30.

The opening 33 may further be in fluid communication with at least one window 40 between the arms 32 of the body portion via the central part of the body portion. In this way, multiple routes may be provided for a cleaning fluid to enter/leave the central part of the body portion, making the trial neck 30 easier to clean. For instance, a cleaning fluid entering the body portion through the opening 33 may then exit the body portion through one or more of the windows 40 (or vice versa), having performed its cleaning function.

In some embodiments, the bore 39 located at the distal end of the trial neck 30 for receiving the spigot 20 of the broach 10 may be coaxial with, and in fluid communication with, the opening 33 located at the proximal end of the trial neck. Again, this can further improve the cleanability of the trial neck 30, by providing additional routes for cleaning fluids flow to and from the central part of the trial neck 30. It may also be useful to be able to view the bore 39 through the opening 33 at the proximal end, e.g. to view the spigot 20 and/or to check that the bore 39 is free of unwanted material such as bone fragments.

In some examples, the base 36 of the trial neck 30 may be provided with a line marking 43. The line marking 43 may be located on an outer surface of the base 36. The line marking 43 comprise an embossed or debossed marking. The line marking 43 may be substantially linear, and may extend in a direction substantially transverse to the neck axis 5. The line marking 43 may be used to indicate the location of a femoral resection plane. For instance, the resection plane may correspond to a resection plane for a next size of broach 10 in a surgical kit comprising the trial neck 30 and a plurality of differently sized broaches 10.

In some embodiments, the trial neck 30 may itself have a spigot 35 that extends distally therefrom to engage with (insert into) a corresponding bore 15 of the broach 10. The spigot 35 may extend distally from the distally facing underside 37 of the base 36 of the trial neck 30. The corresponding bore 15 of the broach 10 may be located at the proximal end of the broach 10. A proximal opening of the bore 15 may be located in the proximally facing surface 14 of the broach. In use, the spigot 35 and corresponding bore 15 may engage to prevent unwanted rotation of the trial neck 30 about the neck axis 5 when the spigot 20 of the broach 10 is received within the bore 39.

As described herein, a trial neck 30 according to embodiments of this invention may include a resilient retaining member configured to engage a surface of the broach 10 when the trial neck 30 is connected to the broach 10, for inhibiting removal of the trial neck 30 from the broach 10. In relation to the Figures, it has been described above that the resilient retaining member may comprise a resilient retaining finger 44 located on a sidewall of a bore 39, which biased inwards towards an axis of the bore 39 to engage with the spigot 20 when the spigot 20 is received within the bore 39. However, it is envisaged that the resilient retaining member may take other forms.

For instance, instead of providing the resilient retaining member as a resilient retaining finger 44 for engaging with the spigot 20 of the broach 10, the resilient retaining member may be provided on the spigot 35, for engaging with a side wall of the corresponding bore 15 of the broach 10 when the trial neck 30 is connected to the broach 10. It is envisaged that in some examples, the spigot 35 may include a plurality of such resilient retaining members. The resilient retaining members may comprise elongate fingers that extend along at least part of the length of the spigot 35. The resilient retaining members may be separated by one or more elongate slots. The resilient retaining members may be resiliently deflectable inwards towards a central axis of the spigot 35 on insertion of the spigot 35 into the corresponding bore 35 of the broach 10. Once inserted into the corresponding bore 15, the resilient retaining members of the spigot 35 may engage with (e.g. urge outwardly against) the inner sidewall of the bore 15, thereby to retain the spigot 35 within the bore 15, to inhibit removal of the trial neck 30 from the broach 10.

Accordingly, it will be appreciated that the spigot 35 may be configured similarly to the connection members 34 of the male connector at the proximal end of the trial neck 30, which insert into a female connector of the aforementioned trial head. The resilient retaining members of the spigot 35 may extend distally from, and may be integrally formed with, a base of the spigot 35. The base of the spigot 35 and the resilient retaining members may form a live hinge.

It is envisaged that the two kinds of resilient retaining members described above may be both be including in a trial neck 30 according to an embodiment of this invention. Accordingly, it is envisaged that a trial neck 30 may include one or more resilient retaining members on a spigot 35 thereof for engaging with an inner surface of a bore 15 of the broach 10 and/or one or more resilient retaining members (e.g. fingers 44) for engaging with a spigot 20 of the broach 10.

A trial neck 30 of the kind described herein may be provided a part of a surgical kit for a hip replacement procedure. For instance, the surgical kit may include one or more trial necks 30 of the kind described above, where at least two of the trial necks 30 are a different size and/or have a different neck offset. The surgical kit may also include one or more broaches, for instance of different sizes. The surgical kit may further include one or more trial heads, which again may be of different sizes.

A hip replacement procedure may include use of a trial neck 30, broach 10 and trial head of the kind described above. The combination of the trial neck 30, broach 10 and trial head may be used to trial for a femoral implant having a given size, neck offset, amount of anteversion etc. By providing a surgical kit having one or more trial necks 30, broaches 10 and trial heads having different sizes, offsets, amounts of anteversion etc., a kit comprising a trial neck 30 of the kind described herein can be used to determine the correct configuration for the femoral implant that is to be used in the subsequent procedure.

In accordance with an embodiment of this invention, a method for trialling a neck of an orthopedic implant in a hip replacement procedure may include removing the neck and head of the femur, gaining access to the medullary canal, and then using tools such as reamers and/or broaches to shape the medullary canal and a proximal entrance to the canal to receive a stem of the implant. To perform the trialling process, a broach 10 of the kind described above may be inserted into the medullary canal, and then one or more combinations of trial necks 30 and/or trial heads of the kind described above may be attached to the broach 10 while the surgeon determines the correct configuration (size, offset, anteversion amount etc.) of the implant to the used in the replacement hip.

Where the trial neck 30 includes a male connector of the kind described above located at the proximal end of thereof, the trialling process may include inserting the male connector into a corresponding female connector of one or more trial heads. As described previously, on insertion of the connection members of the male connector into the female connector of the trial head(s), the connection members 34 of the male connector are resiliently deflected inwards towards the neck axis 5.

Where the trial neck 30 includes one or more resilient retaining members of the kind described above, these resilient retaining members may engage a surface of the broach 10 as the surgeon connects the trial neck 30 to the broach 10, for inhibiting removal of the trial neck 30 from the broach 10. As noted above, the one or more resilient retaining members may be implemented as one or more resilient retaining fingers 44 located in a bore 39 of the trial neck 30, and/or as one or more elongate fingers that extend along at least part of the length of a spigot 35 that extends distally from a distal end of the trial neck 30.

Where the trial neck 30 includes a body portion of the kind described above, having a frame with a plurality of arms 32 extending along the neck axis 5, the trialling procedure may include viewing at least part of a connection feature of the trial neck 30 between the arms 32 of the frame for verifying correct connection of the trial neck 30 to the broach 10. The connection feature may be located in the central part of the body portion of the trial neck 30 as noted previously. The connection feature(s) viewed by the surgeon in this part of the trialling process may include, for instance, one or more of:

the boss 38 (e.g. the angled surface 31, and/or the laterally located opening on a side wall of the boss 38),
the bore 39 (e.g. a proximal open end of the bore 39 located in the central part of the body portion),
the spigot 20 (e.g. the chamfered surface 23 located at a proximal end of the spigot 20),
the notch 21, and/or
the resilient retaining finger 44.

The trialling process may also include viewing an indicium 19 located on a proximal end of the spigot 20, e.g. to determine the type of broach 10 that is currently inserted in the medullary canal of the femur. The surgeon may view the indicium through the arms 32 of the frame as noted above. The trialling process may also include viewing an indicium located on a surface of the trial neck 30 in the central part of the body portion (e.g. the indicium 48 described above) e.g. to determine the type, size or angular offset of the trial neck 30 that is currently connected to the broach 10.

As noted above, the trial neck 30 used in the hip replacement procedure may have a substantially hollow body portion that extends along the neck axis 5 between the distal end and the proximal end. This can reduce the weight of the trial neck 30, making it easier to handle during the procedure.

After the trialling is complete, the trial head(s), trial neck(s) 30 and broach(es) 10 may be removed and the appropriate implant, as determined during the trialling process may be installed.

After the trial head(s), trial neck(s) 30 and broach(es) 10 have been used, the hip replacement procedure may further include cleaning them. During cleaning of each trial neck 30 of the kind described above, features of the trial neck such as:

the window(s) 40,
the opening 33 in fluid communication with the central part of the body portion, which may be in fluid communication one or more of the windows 40, and/or
the bore 39, may, as previously described aid with the cleaning process. It is envisaged that these benefits may similarly arise during cleaning of the trial neck 30 prior to the hip replacement procedure.

Figure 14:
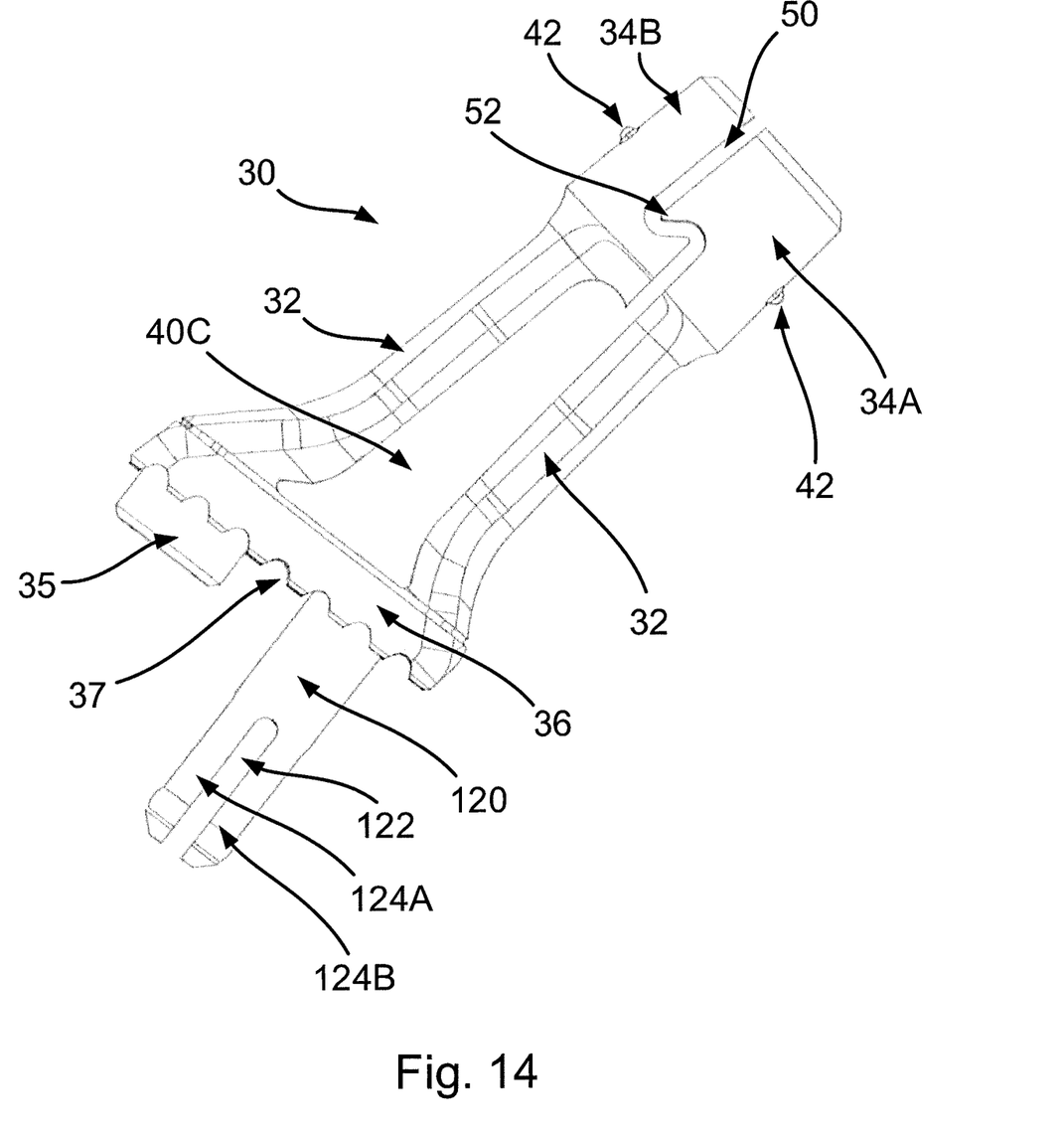
FIG. 14 shows a trial neck in accordance with a further embodiment of the invention.
Figure 15:
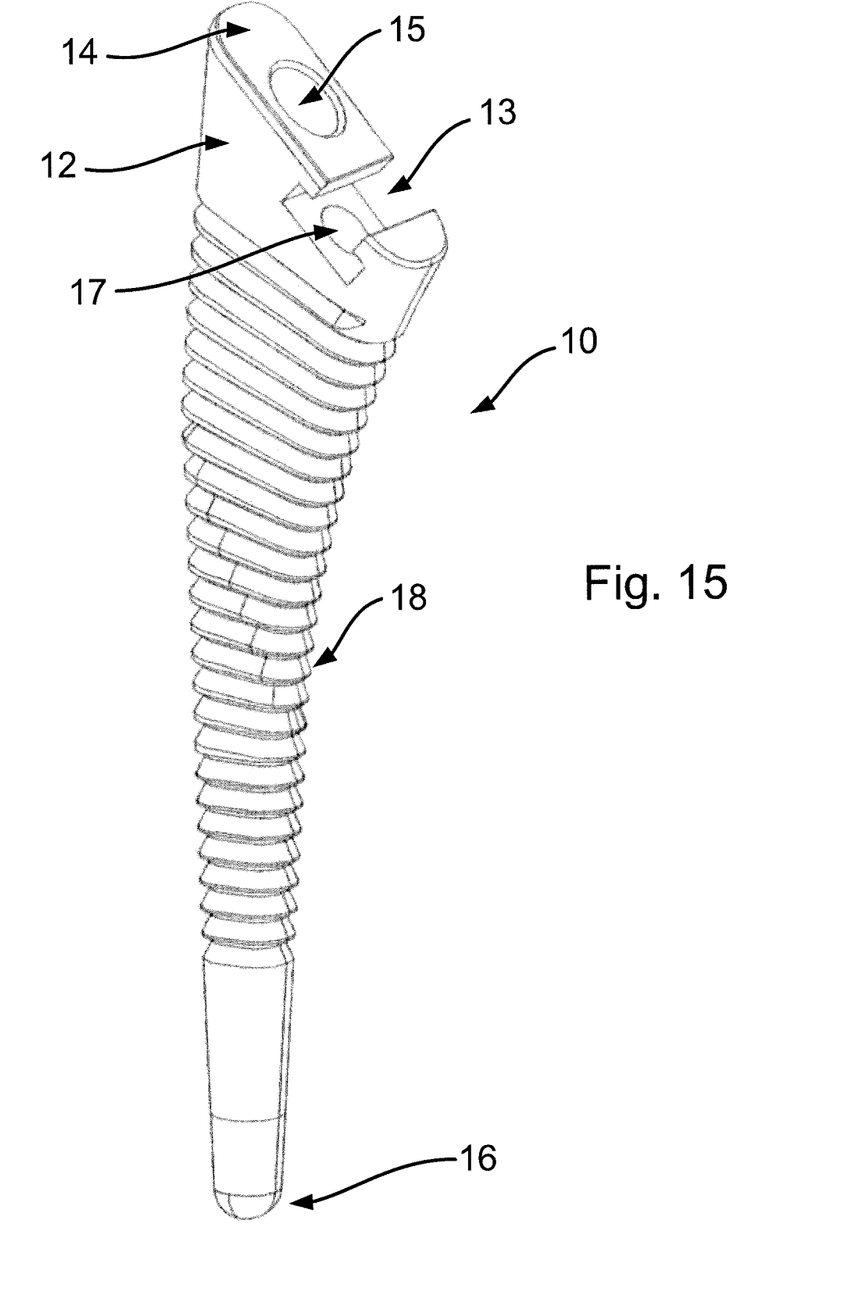
FIG. 15 shows a broach for use with the trail neck of FIG. 14 in accordance with a further embodiment of the invention.
Figure 16:
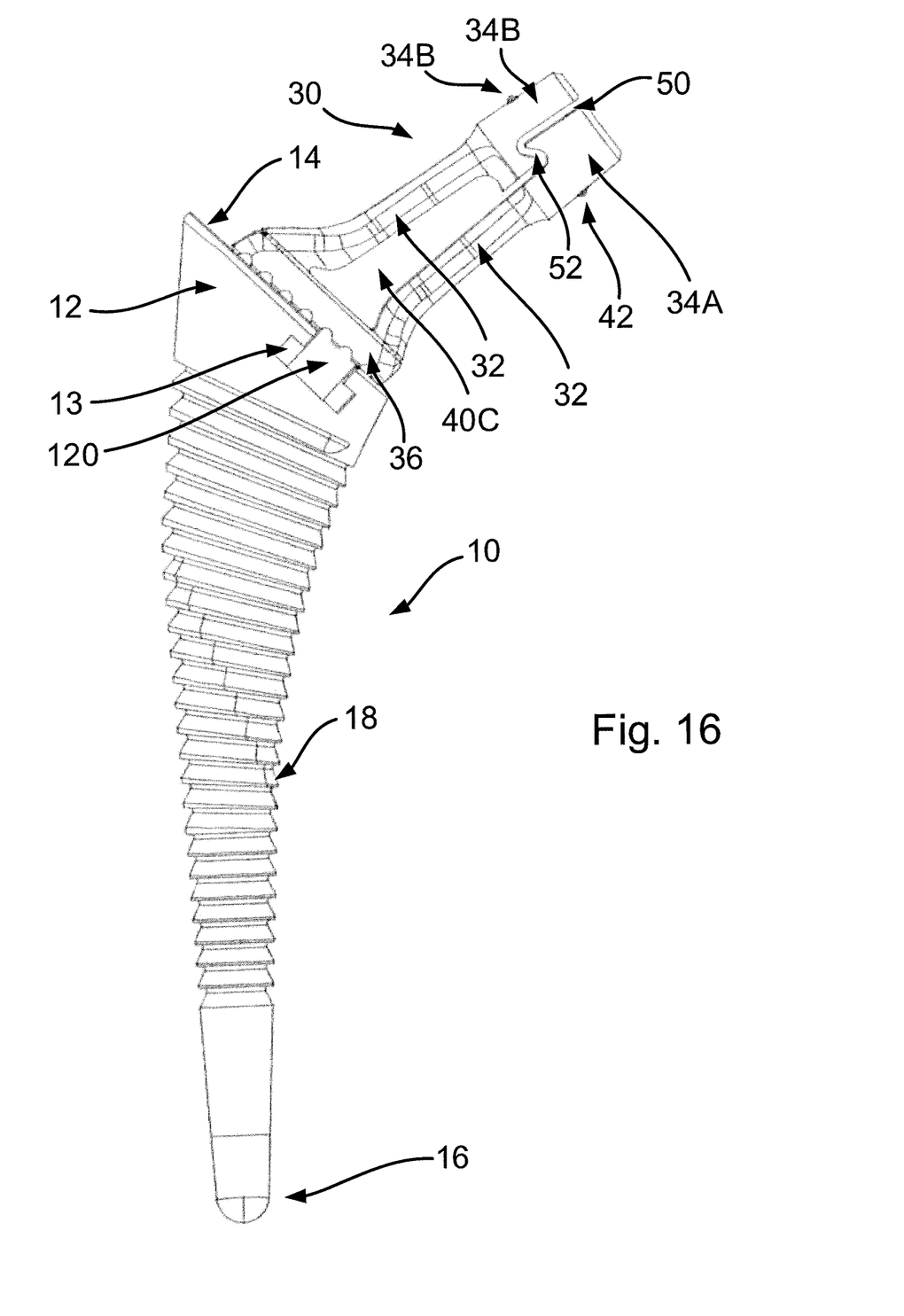
FIG. 16 shows the trial neck of FIG. 14 connected to the broach of FIG. 15 in accordance with an embodiment of the invention.

FIG. 14 shows a trial neck 30 in accordance with another embodiment of this invention. FIG. 15 shows a broach 10 for use with the trail neck 30 of FIG. 14. FIG. 16 shows the trial neck of FIG. 14 connected to the broach 10 of FIG. 15 in accordance with an embodiment of the invention.

The trial neck 30 in this embodiment may share a number of features in common with the embodiment described above in relation to FIGS. 1 to 13. As will be appreciated from the description of FIGS. 14 to 15 below, the present embodiment differs from the embodiment described above in relation to FIGS. 1 to 13 in the way that the trial neck 30 connects to the broach 10.

The trial neck 30 includes a proximal end and a distal end. As described previously, a body portion of the trial neck 30 may extend between the distal end and the proximal end. Again, the body portion may be substantially hollow. In the present embodiment, as described above, the body portion comprises a frame having a number of arms 32. In particular, in this example, the frame has four arms 32, which define a medial window 40A, a lateral window 40B and an anterior window 40C and a posterior window 40D as described in relation to the first embodiment. The trial neck 30 may also include a number of male connection members 34 separated by one or more slots 50. These slots 50 may include one or more kinks 52 as shown in FIG. 14. As noted already in respect of the first embodiment, this arrangement can allow the proximal end of the trial neck 30 to be connected with the female connection of a trial head. Again, the connection members 34 may be provided with protuberances 42.

As shown in FIG. 14, the distal end of the trial neck 30 may include a base 36, from which the arms 32 may extend proximally. The distal end of the trial neck 30 may be connected to the proximal end of the broach 10 as will be described in more detail below in relation to FIG. 16.

In the present embodiment, the distally facing underside 37 of the base 36 includes a plurality of grooves (these can be seen in FIGS. 14 and 16). As noted above, grooves of this kind may reduce the surface contact between the base 36 and a build plate of a 3D print machine during manufacture, for making the part easier to remove from a 3D printer, thereby reducing manufacturing costs.

In the present embodiment, the trial neck 30 includes a spigot 35, which may be similar to the spigot 35 described above in relation to the first embodiment. In particular, the spigot 35 can extend distally from the distally facing underside 37 of the trial neck 30 to be received in a corresponding bore 15 (see FIG. 15) of the broach 10. The spigot 35 and the bore 15 may be configured similarly to those described above in relation to the first embodiment.

In the present embodiment, unlike the first embodiment, the trial neck 30 also includes a spigot 120, which extends distally from the distally facing underside 37 of the trial neck 30. This spigot 120 can be received in a corresponding bore 17 of the broach 10 (see FIG. 15). In the present embodiment, the spigot 35 is located laterally with respect to the spigot 120 and the spigot 120 is located medially with respect to the spigot 35. However, it is envisaged that this arrangement could be reversed so that the spigot 120 is located laterally with respect to the spigot 35 and the spigot 35 is located medially with respect to the spigot 120. Note that the provision of the two spigots 35, 120 can act to oppose rotation of the trial neck 30 about the neck axis while the trial neck 30 is attached to the broach 10.

As can be seen in FIG. 15, the proximally facing surface 14 of the broach 10 in this embodiment may include a recessed portion 13. The bore 17 may be located at a base of the recessed portion 13. In this way, the engagement and insertion of the spigot 120 into the bore 17 can be more easily observed by the surgeon. For instance, the recessed portion may allow the rim of the bore 17 to be viewed anteriorly and posteriorly, even when the base 36 of the trial neck 30 is fully seated of the proximally facing surface 14 of the broach 10.

As described herein, in accordance with embodiments of this invention, the trial neck 30 may include a resilient retaining member that is configured to engage a surface of the broach 10 when the trial neck 30 is connected to the broach 10, for inhibiting removal of the trial neck 30 from the broach 10. As with the first embodiment described above in relation to FIGS. 1 to 13, it is envisaged that one or more resilient retaining members of this kind may be provided on the spigot 35 for engagement with an inner surface of the bore 15.

In the present embodiment though, and as shown in FIG. 14, the spigot 120 is provided with one or more resilient retaining members 124. Although in the present embodiment only the spigot 120 is provided with resilient retaining members, it is envisaged that both the spigot 35 and the spigot 124 may be provided with resilient retaining members of the kind described herein, for improving the secureness of the attachment between the trail neck 30 and the broach 10.

In the present embodiment, the spigot 120 has two resilient retaining members 124A, 124B. The resilient retaining members 124 may be separated by one or more slots. In the present embodiment, the resilient retaining members 124A, 124B are separated by a single slot 122. When more than two resilient retaining members 124 are provided, more than one slot may also be present, each slot separating a respective pair of the resilient retaining members.

The ends of the resilient retaining members 124A, 124B may have a slightly larger diameter than the spigot 120 as a whole as shown in FIG. 14. The ends of the resilient retaining members 124A, 124B may also be chamfered to aid their insertion into the bore 17 of the broach 10. Insertion of the spigot 120 into the bore 17 urges the members 124A, 124B together. When the spigot 120 is inserted in the bore 17, the resilient retaining members 124A, 124B urge outwardly to engage with the inner surfaces of the bore 17, thereby to inhibit removal of the trial neck 30 from the broach 10.

As with the resilient retaining member(s) of the spigot 35, the resilient retaining members 124A, 124B may comprise elongate fingers that extend along at least part of the length of the spigot 120. It is envisaged that the spigot may include a single resilient retaining member, or indeed more than two resilient retaining members.

Accordingly, it will be appreciated that the spigot 120 may be configured similarly to the connection members 34 of the male connector at the proximal end of the trial neck 30, which insert into a female connector of the aforementioned trial head. The resilient retaining members of the spigot 120 may extend distally from, and may be integrally formed with, a base of the spigot 120. The base of the spigot 120 and the resilient retaining members may form a live hinge.

It will be appreciated from a comparison of FIGS. 14-16 with FIGS. 1-13 that in the present embodiment, the arrangement of the spigot 120 and bore 17 is generally inverted with respect to the arrangement of the spigot 20 and the bore 39. Accordingly, in the present embodiment, it is noted that the trial neck 30 need not be provided with a boss 38 of the kind shown in FIGS. 1-13, which may simplify the construction of the trial neck 30. Note that in the absence of a boss 38, other parts of the interior of the body portion of the trial neck 30 may have improved visibility, for instance for viewing features such as markings or indicia as explained previously.

As shown in FIG. 15, the broach 10 for use with the trial neck 30 shown in FIG. 14 may be similar in many respects to the broach 10 described above in relation to the first embodiment. For instance, the broach 10 may include a distal end having a tip 16 and a proximal end 12 having a proximally facing surface 14. The broach may also have an outer surface having a plurality of teeth 18 or other cutting edges. However, as described above, the features provided in the broach 10 for connection with the features of the trial neck 30 may differ from those described above in relation to the first embodiment.

Accordingly, there has been described a trial neck and a method for trialling a neck of an orthopedic implant in a hip replacement procedure. The method includes inserting a broach into a medullary canal of a femur and connecting a distal end of a trial neck to a proximal end of the broach. The trial neck includes a proximal end connectable to a trial head. The trial neck includes a body portion extending along a neck axis of the trial neck between the distal end and the proximal end. The proximal end includes a male connector for connection to a corresponding female connector of a trial head. The male connector includes a plurality of connection members extending parallel to the neck axis. The connection members are separated by one or more elongate slots including at least one kink forming an interlock between the connection members separated by that slot. The connection members are resiliently deflectable.

Although particular embodiments of the invention have been described, it will be appreciated that many modifications/additions and/or substitutions may be made within the scope of the claimed invention.

The invention claimed is:

1. A trial neck for use in a hip replacement procedure, the trial neck comprising:
 a proximal end;
 a distal end connectable to a proximal end of a broach; and
 a body portion extending along a neck axis of the trial neck between the distal end and the proximal end, wherein the proximal end of the trial neck includes a male connector for connection to a corresponding female connector of a trial head, wherein the male connector comprises a plurality of connection members extending substantially parallel to the neck axis, wherein the connection members are separated by one or more elongate slots, wherein the connection members are resiliently deflectable inwards towards the neck axis on insertion of the male connector into the female connector of the trial head, and wherein the or each slot of the male connector includes at least one kink forming an interlock between the connection members separated by that slot, to prevent over-deflection of the connection members in a direction towards and/or away from the neck axis.

2. The trial neck of claim 1, wherein the body portion comprises a frame having a plurality of arms extending along the neck axis between the distal end and the proximal end of the trial neck, wherein each connection member of the male connector is integrally formed with a proximal end of one or more respective arms of the body portion.

3. The trial neck of claim 2, wherein each elongate slot opens out into one or more windows located between the arms of the frame.

4. The trial neck of claim 2, wherein the male connector comprises exactly two connection members, wherein the frame of the body portion comprises exactly four arms, and wherein each connection member is integrally formed with two of said arms.

5. The trial neck of claim 2, wherein a central part of the body portion is visible between the arms of the frame.

6. The trial neck of claim 2, wherein the distal end of the trial neck comprises a base having a distally facing underside connectable to the proximal end of the broach, wherein the arms of the frame of the body portion extend proximally from the base towards the proximal end of the trial neck.

7. The trial neck of claim 6, wherein the arms of the body portion are integrally formed with the base.

8. The trial neck of claim 7, wherein the base and the arms of the frame form a live hinge for said resilient deflection of the connection members of the male connector towards the neck axis.

9. The trial neck of claim 1, wherein the at least one kink forms zigzag-shaped interlock.

10. The trial neck of claim 1, manufactured by 3D printing.

11. A surgical kit for a hip replacement procedure, the kit comprising:
    one or more trial necks of claim 1, wherein at least two of the trial necks are a different size and/or have a different neck offset;
    one or more said broaches; and
    one or more said trial heads.

* * * * *